(12) United States Patent
Jitoe et al.

(10) Patent No.: US 6,595,976 B2
(45) Date of Patent: Jul. 22, 2003

(54) DISPOSABLE PULL-ON DIAPER

(75) Inventors: Yoshikazu Jitoe, Kagawa-ken (JP); Nariaki Shimoe, Kagawa-ken (JP); Yoshinori Kumasaka, Kagawa-ken (JP)

(73) Assignee: Uni-Charm Corp., Ehime-ken (JP)

( * ) Notice: Subject to any disclaimer, the term of this patent is extended or adjusted under 35 U.S.C. 154(b) by 0 days.

(21) Appl. No.: 09/410,200

(22) Filed: Sep. 30, 1999

(65) Prior Publication Data
US 2002/0151862 A1 Oct. 17, 2002

(30) Foreign Application Priority Data
Oct. 2, 1998 (JP) .................................. 10-281703

(51) Int. Cl.⁷ ................................................ A61F 13/15
(52) U.S. Cl. ................................ 604/385.29; 604/385.3
(58) Field of Search ................................ 604/367, 372, 604/385.01, 385.23–385.29, 385.3, 386, 392, 396

(56) References Cited

U.S. PATENT DOCUMENTS

| | | |
|---|---|---|
| 4,692,163 A | 9/1987 | Widlund et al. |
| 5,163,932 A * | 11/1992 | Nomura et al. .......... 604/385.2 |
| 5,447,508 A | 9/1995 | Numano et al. |
| 5,645,543 A * | 7/1997 | Nomura et al. .......... 604/385.2 |
| 5,735,839 A | 4/1998 | Kawaguchi et al. |
| 5,749,865 A * | 5/1998 | Yamamoto et al. ...... 604/385.2 |
| 5,876,392 A * | 3/1999 | Hisada ..................... 604/385.2 |
| 5,916,206 A * | 6/1999 | Ostubo et al. ........... 604/385.2 |
| 5,941,865 A * | 8/1999 | Ostubo et al. ........... 604/385.2 |
| 6,049,916 A * | 4/2000 | Rajala et al. .................. 2/400 |

FOREIGN PATENT DOCUMENTS

| | | |
|---|---|---|
| EP | 0 641 552 A1 | 3/1995 |
| EP | 0 761 193 A2 | 3/1997 |
| EP | 0 873 738 A2 | 10/1998 |
| EP | 0 875 226 A2 | 11/1998 |
| JP | B-7-44945 | 5/1995 |
| JP | A-7-236650 | 9/1995 |
| JP | A-9-84826 | 3/1997 |
| WO | WO 97/22318 | 6/1997 |

OTHER PUBLICATIONS

Copy of European Search Report dated Mar. 7, 2001.

* cited by examiner

*Primary Examiner*—Dennis Ruhl
*Assistant Examiner*—Jamisue A. Webb
(74) *Attorney, Agent, or Firm*—Butzel Long

(57) ABSTRACT

A disposable pull-on diaper includes a topsheet, a backsheet and an absorbent core disposed therebetween. In any one of front and rear waist regions of the diaper, second elastic members are disposed between the core and the backsheet to extend under tension circumferentially of the waist region and secured to the inner surface of the backsheet only at their portions extending outward beyond transversely opposite side edges.

10 Claims, 4 Drawing Sheets

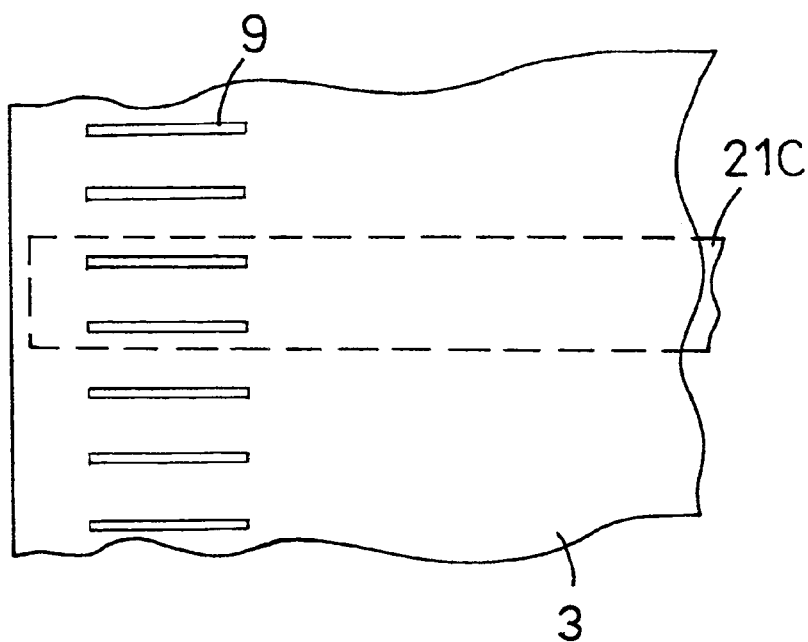
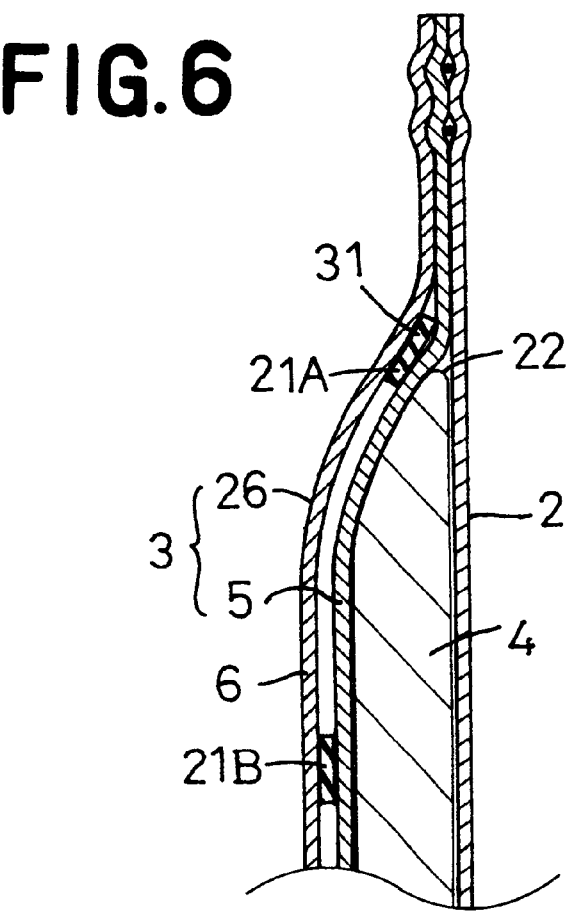

DISPOSABLE PULL-ON DIAPER

BACKGROUND OF THE INVENTION

The present invention relates to a disposable pull-on diaper for absorption and containment of bodily wastes.

Japanese Patent Application Disclosure Gazette (Kokai) No. Hei7-236650 discloses a disposable pull-on diaper including elastic members extending circumferentially of front and rear waist regions. Portions of these elastic members extending across a liquid-absorbent core of the diaper have an elongation less than 1.3 (i.e., substantially without any tension) and are secured to a backsheet of the diaper. Portions of the elastic members extending outward beyond transversely opposite side edges of the absorbent core have an elongation of 1.3 or higher and are secured also to the backsheet.

Japanese Patent Publication Gazette (Kokoku) No. Hei7-44945 discloses a disposable pull-on diaper including a plurality of elastic members extending circumferentially of front and rear waist regions across a liquid-absorbent core of the diaper so as to form a plurality of gathers in a zone overlying the absorbent core.

Japanese Patent Application Disclosure Gazette (Kokai) No. Hei9-84826 discloses a disposable pull-on diaper including a plurality of thread-like elastic members extending circumferentially of front and rear waist regions arranged so that these elastic members may be placed upon longitudinally opposite ends of a liquid-absorbent core of the diaper from outside the absorbent core.

The invention disclosed in the Japanese Patent Application Disclosure Gazette (Kokai) No. Hei7-236650 claims an advantageous effect such that the portions of the elastic members extending across the absorbent, core may be put substantially free from a tension so as to prevent the absorbent core from being wrinkled or position-shifted as the elastic members contract. However, the portions extending across the absorbent core can not function to press the absorbent core against the wearer's body as they contract, since the portions are joined to the backsheet substantially without any tension. Accordingly, it is difficult for the diaper to assure a significant leakage preventing effect by a good fitting of the absorbent core to the wearer's body.

Moreover, the invention is accompanied with a problem that the manufacturing process should include complicated steps of placing the elastic members partially in a tensioned state and partially in a non-tensioned state.

The invention disclosed in the Japanese Patent Publication Gazette (Kokoku) No. Hei7-44945 certainly describes an effect to place the liquid-absorbent core against the wearer's body with a good fitting but does not disclose how to arrange these elastic members in the front and rear waist regions. Even if this problem is put aside, formation of gathers in the zone overlying the liquid-absorbent core not only may deteriorate a smooth touch of the diaper but also may form similar gathers on the absorbent core also. These gathers formed on the absorbent core may deteriorate its fitting to the wearer's body and prevent body fluids from being rapidly absorbed.

The invention disclosed in the Japanese Patent Application Disclosure Gazette (Kokai) No. Hei9-84826 is certainly effective to restrain the longitudinally opposite ends of the absorbent core from being curved away from the wearer's body. However, in order to widen a range over which the foresaid effect is obtained, the number of these elastic members must be correspondingly increased and properly arranged in the vicinity of the ends of the absorbent core. In consequence, the manufacturing process must be correspondingly complicated.

SUMMARY OF THE INVENTION

It is an object of the present invention to provide a disposable pull-on diaper improved to solve the foresaid various problems.

According to the present invention, there is provided a disposable pull-on diaper having a front waist region, a rear waist region and a crotch region therebetween, the diaper comprising a liquid-pervious topsheet, a liquid-impervious backsheet and a liquid-absorbent core disposed between the topsheet and the backsheet, the front and rear waist regions being joined to each other along transversely opposite side edges thereof so as to form a waist-opening and a pair of leg-openings, the waist-opening being provided with a plurality of first elastic members and the leg-openings also being provided with elastic members, respectively, the elastic members extending under tension along peripheral edges of the waist-opening and leg-openings, wherein a plurality of second elastic members extend across the absorbent core at least in one of the front and rear waist regions between transversely opposite side edges of the waist region.

The disposable pull-on diaper of the present invention a plurality of second elastic members are such that any one of them presents a stretch stress lower than a stretch stress presented by any one of the first elastic members and extend across the absorbent core on an outer surface thereof with portions of the second elastic members which extend outward beyond the transversely opposite side edges of the absorbent core being secured to the backsheet and other portions thereof which extend between the transversely opposite side edges of the absorbent core being secured neither to the backsheet nor to the absorbent core.

Preferred but non-limiting embodiments of the present invention are enumerated hereunder.

(1) The second elastic members are secured to the backsheet only in the vicinity of zones in which the front and rear waist regions are joined to each other along their respective side edges.

(2) The backsheet is made of a thermoplastic synthetic resin film and the second elastic members are secured to the inner surface of the film.

(3) The backsheet comprises a thermoplastic synthetic resin film and a nonwoven fabric bonded to the outer surface of the film so that the second elastic members may be disposed between the film and the nonwoven fabric and secured to the outer surface of the film or the inner surface of the nonwoven fabric.

(4) The inner surface of the backsheet is joined to the outer surface of the absorbent core.

(5) The second elastic members are provided in the form of ribbons each having a width of 3~20 mm.

(6) The absorbent core has front and rear ends lying in the front and rear waist regions, respectively, and the second elastic members cover at least one of the front and rear ends inclusive of its vicinity in a direct or indirect manner.

(7) The absorbent core has a Gurley Stiffness Value of 0.5~2 g and the second elastic members present a total stretch stress of 100~230 gf.

(8) The crotch region is provided with a third elastic member extending under tension across the absorbent core in parallel to the second elastic members.

BRIEF DESCRIPTION OF THE DRAWINGS

FIG. 4 is a diagram showing, in an enlarged scale, a part of FIG. 1;

FIG. 6 is a sectional view taken along a line VI—VI in FIG. 5.

DETAILED DESCRIPTION OF THE PREFERRED EMBODIMENTS

Details of a disposable pull-on diaper according to the present invention will be more fully understood from the description given hereunder with reference to the accompanying drawings.

Figure 1:
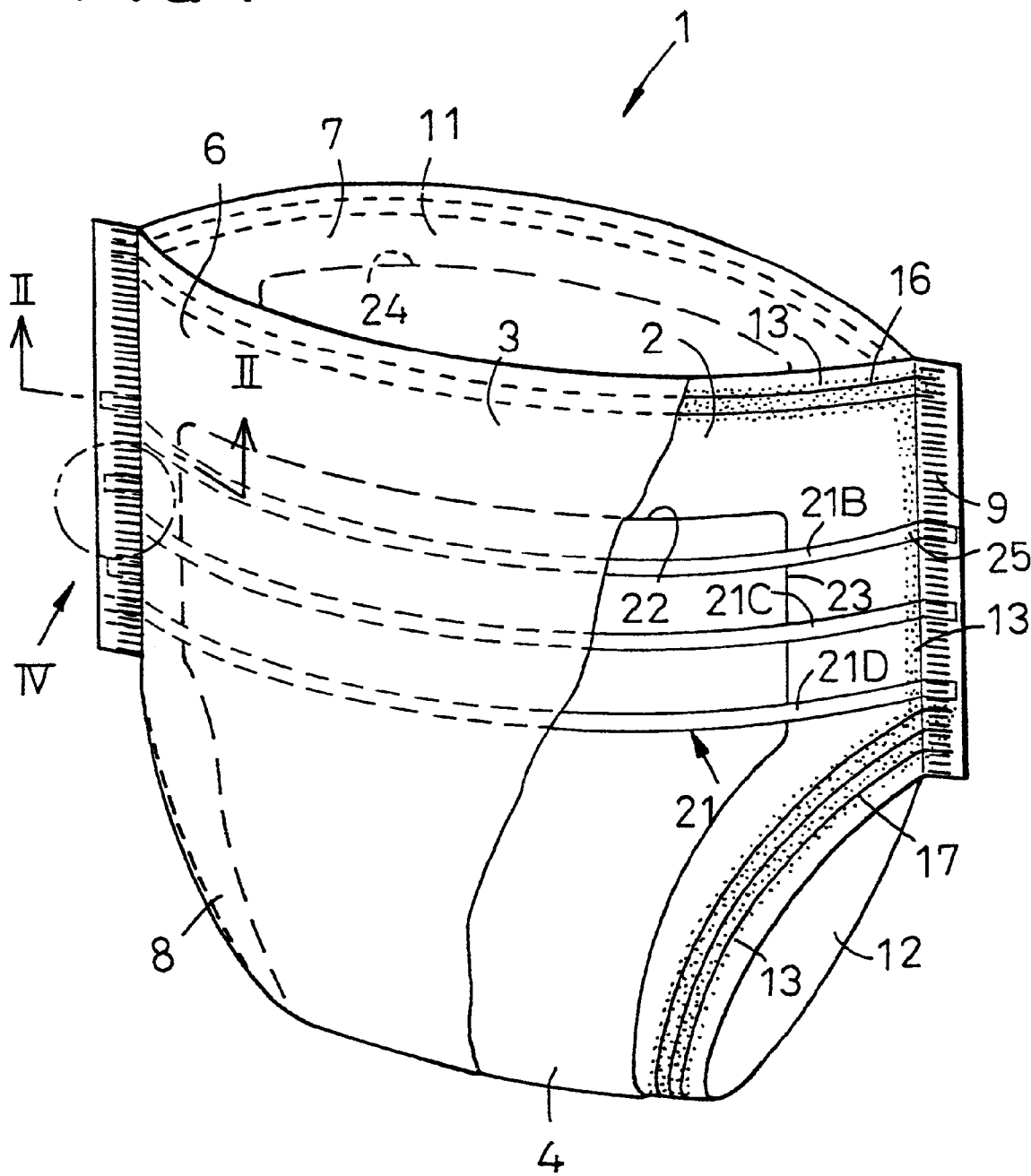
FIG. 1 is a perspective view showing a partly cutaway disposable pull-on diaper according to one embodiment of the present invention.

A partly cutaway disposable pull-on diaper 1 shown by FIG. 1 in a perspective view comprises a liquid-pervious topsheet 2 formed by a nonwoven fabric of thermoplastic synthetic fibers, a liquid-impervious backsheet 3 formed by a thermoplastic synthetic resin film and a liquid-absorbent core 4 disposed between these two sheets 2, 3. The diaper 1 has a front waist region 6, a rear waist region 7 and a crotch region 8 extending between these two waist regions 6, 7. The front and rear waist regions 6, 7 are put flat one upon another and joined together along their respective side edges at a plurality of heat-sealing zones 9 intermittently arranged along the respective side edges so as to form a waist-opening 11 and a pair of leg-openings 12. In the front and rear waist regions 6, 7 as well as in the crotch region 8, the topsheet 2 and the backsheet 3 extend outward beyond a peripheral edge of the absorbent core 4 and are placed upon and joined to each other by means of hot melt adhesive 13 along a peripheral edge of the diaper 1.

The diaper 1 has elastic members 16, 17 extending along peripheral edges of the waist-opening 11 and the leg-openings 12, respectively. These elastic members 16, 17 are disposed between the topsheet 2 and the backsheet 3 and secured under tension to the inner surface of at least one of these two sheets 2, 3 by means of the adhesive 13 or adhesive provided separately of the adhesive 13.

The diaper 1 further includes a plurality of auxiliary elastic members 21 (21B, 21C, . . . ) extending in parallel one to another circumferentially of the diaper 1 across at least one of the front and rear waist regions 6, 7. Each of these auxiliary elastic members 21 presents a stretch stress lower than a stretch stress presented by each of the waist-opening's elastic members 16 and extends across the absorbent core 4 on its outer surface. According to the illustrated embodiment, three elastic members 21B, 21C, 21D extend across the absorbent core 4, between the inner surface of the backsheet 3 and the outer surface of the absorbent core 4, to the transversely opposite side edges of the diaper 1. Assumed that the diaper 1 has the auxiliary elastic members 21 in the front waist region 6 as well as in the rear waist region 7, two different modes of realization will be possible: The corresponding elastic members 21 in the front and rear waist regions 6, 7 extend along the same levels of the diaper 1 so as to be placed upon each other at the side edges of the diaper 1 and to form loops, respectively. On the other hand, the corresponding elastic members 21 in these two waist regions 6, 7 may extend along different levels of the diaper 1 and, therefore, the loops are not formed.

The portions of the auxiliary elastic members 21 extending outward beyond transversely opposite side edges 23, 23 of the absorbent core 4 are secured to the inner surface of the backsheet 3 and preferably secured to the inner surface of the backsheet 3 only at the transversely opposite side edges of the diaper 1 by means of adhesive 25 and/or by means of the heat-sealing zones 9. The auxiliary elastic members 21 are secured neither to the backsheet 3 nor to the absorbent core 4 in the area defined between the transversely opposite side edges 23, 23 of the absorbent core 4.

Figure 2:
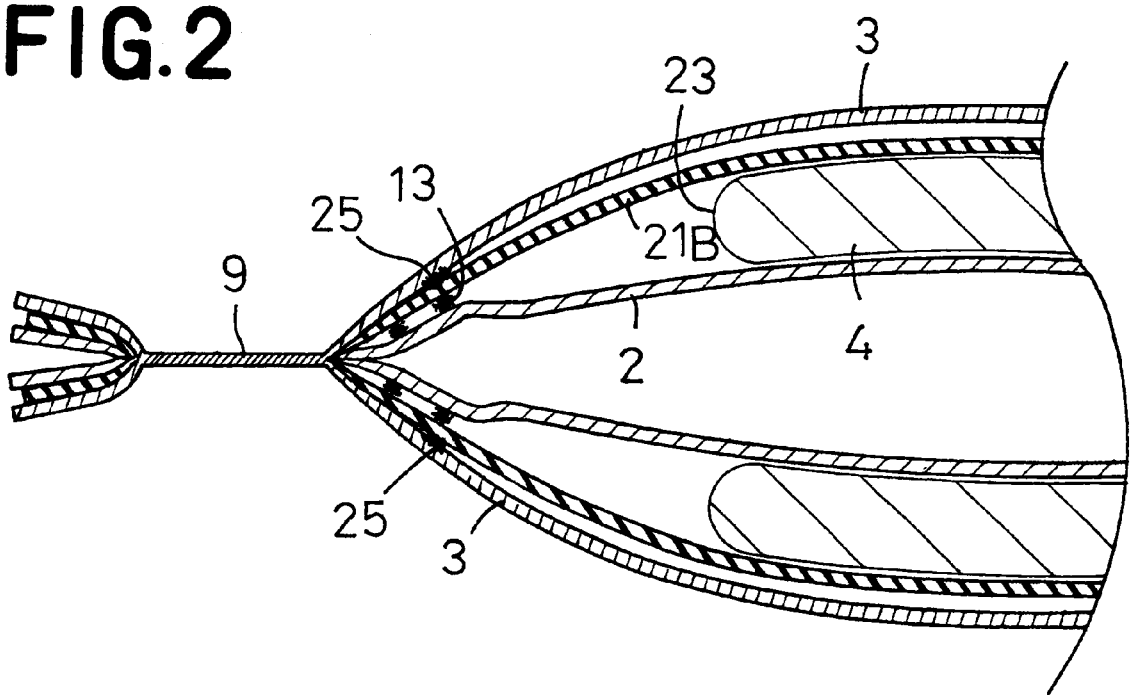
FIG. 2 is a sectional view taken along a line II—II in FIG. 1.

FIG. 2 is a fragmentary sectional view taken along a line II–II in FIG. 1, exemplarily illustrating a manner in which the auxiliary elastic member 21B extending across the absorbent core 4 is secured to the inner surface of the backsheet 3. As will be apparent from FIG. 2, the elastic member 21B uniformly tensioned transversely of the diaper 1 has its opposite ends secured to the inner surface of the backsheet 3 along the respective arrays of the heat-sealing zones 9, respectively, and its portions defined between respective the ends and respective the side edges 23 are joined to the inner surface of the backsheet 3 by means of the hot melt adhesive 25. When the topsheet 2 and the backsheet 3 are joined to each other along the side edges of the diaper 1 by means of the hot melt adhesive 13, the elastic members 21 are also secured to the inner surface of the topsheet 2 by means of the adhesive 13.

Along the arrays of the heat-sealing zones 9, the topsheet 2 and the backsheet 3 of the front and rear waist regions 6, 7, respectively, are placed one upon another and heated to be heat-sealed one with another under pressure. With the arrangement in which the auxiliary elastic members 21 are secured to the backsheet 3 only along the arrays of the heat-sealing zones 9, stock material for the members 21 is preferably selected so that the members 21 can be heat-sealed with the topsheet 2 as well as with the backsheet 3. An example of suitable stock materials is elastomer made of thermoplastic synthetic resin having a melting point similar to that of the topsheet 2 and the backsheet 3.

While a thickness of the auxiliary elastic members 21 is not critical so far as these members 21 can effectively function to press the absorbent core 4 from its outer side against a wearer's body, a width thereof is preferably dimensioned in a range of 3~20 mm. A total stretch stress of the members 21 is preferably in a range of 100~230 gf with respect to the absorbent core 4 having a Gurley Stiffness Value of 0.5~2 g. With the members 21 having a width less than 3 mm, these members 21 may cut into tissue paper (not shown) forming the surface of the absorbent core 4 and deteriorate a body fluid diffusing function expected for the tissue paper. While it is possible to use the members 21 having a width of 20 mm or more, an amount of these members 21 to be used will correspondingly increases and, as a result, the cost for stock material will unnecessarily increases.

With the diaper 1 arranged as has been described above, contraction of the auxiliary elastic members 21 reliably puts the absorbent core 4 tightly against the wearer's body. Since the portions of these auxiliary elastic members 21 extending across the absorbent core 4 are joined neither to the backsheet 3 nor to the absorbent core 4, contraction of these auxiliary elastic members 21 does not cause both the backsheet 3 and the absorbent core 4 to be finely wrinkled. Accordingly, a flat absorbent core may be adopted in this diaper 1 to ensure that the absorbent core 4 can be pressed tightly against the wearer's body without any deformation. Furthermore, the backsheet 3 free from any fine wrinkles can advantageously eliminate the fine wrinkles (gathers) inevitably formed in the waist regions of the diaper which has been one of the problems by the prior art, for example, the Japanese Patent Publication Gazette (Kokoku) No. Hei7-44945 and thereby can provide a smooth touch.

Figure 3:
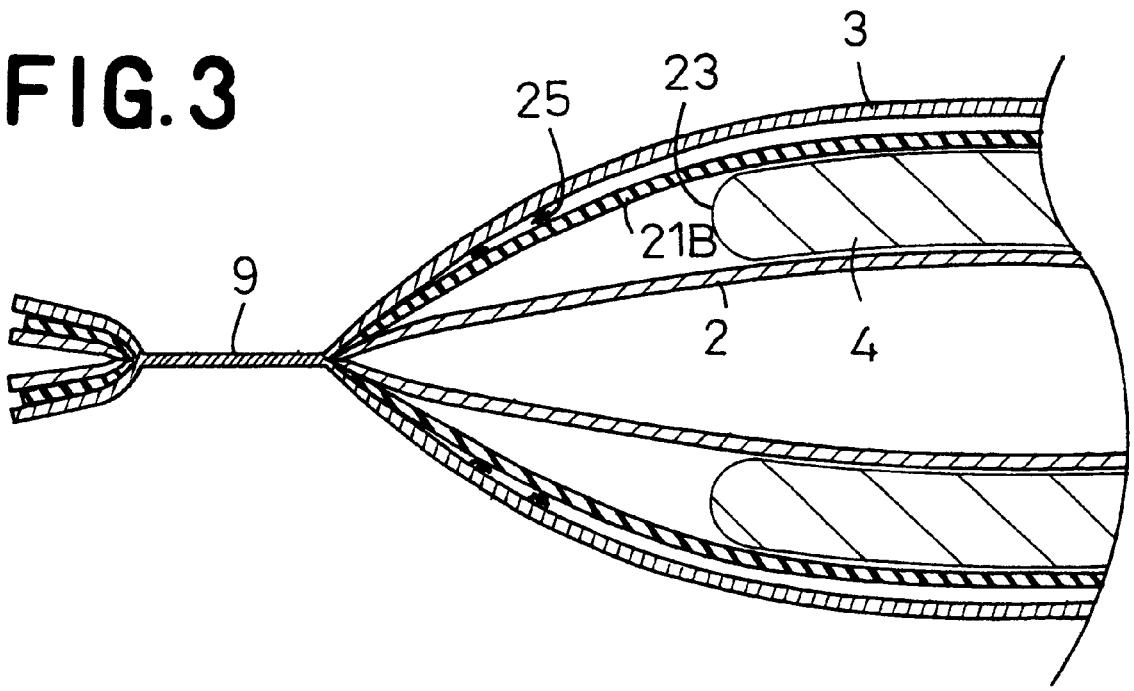
FIG. 3 is a view similar to FIG. 2 showing another embodiment of the present invention.

FIG. 3 is a view similar to FIG. 2 showing the diaper 1 according to another embodiment of this invention. In this embodiment of the diaper 1, the topsheet 2 and the backsheet 3 are joined to each other only along the arrays of the heat-sealing zones 9 instead of being bonded together along their side edges by means of the hot melt adhesive 13. The auxiliary elastic members 21B are joined to the inner surface of the backsheet 3 by means of the adhesive 25.

FIG. 4 is a diagram showing a portion IV encircled by imaginary line in FIG. 1. As shown, the diaper 1 is provided along its side edge with the heat-sealing zones 9 arranged intermittently in a vertical direction and the auxiliary elastic member 21C extends so as to cover a pair of the adjacent heat-sealing zones 9. The member 21C which is relatively wide can be secured to the diaper 1 at two or more heat-sealing zones 9 as shown.

Figure 5:
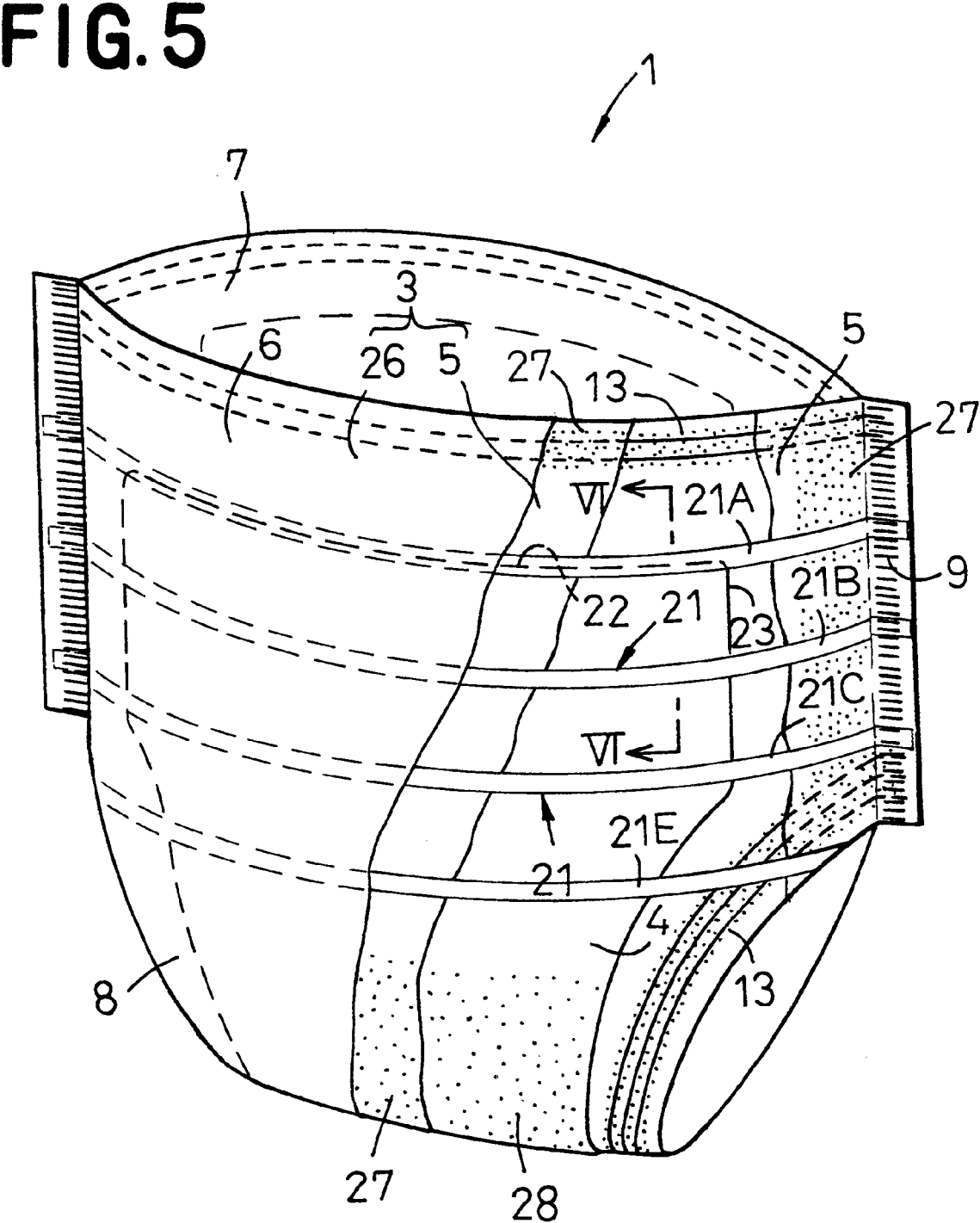
FIG. 5 is a view similar to FIG. 1 showing still another embodiment of this invention.

FIG. 5 is a view similar to FIG. 1 and FIG. 6 is a sectional view taken along a line VI—VI, both showing the diaper 1 according to still another embodiment of the present invention. According to this embodiment, the backsheet 3 comprises liquid-impervious film 5 made of a thermoplastic synthetic resin and nonwoven fabric 26 made of thermoplastic synthetic fibers with which the outer surface of said film 5 is entirely covered. As in the case of the embodiment shown in FIG. 2, the topsheet 2 and the film 5 are joined to each other along the periphery of the diaper 1. The film 5 and the nonwoven fabric 26 are joined to each other along the side edges of the diaper 1 and along the peripheral edge 5 of the waist-opening 11 and the leg-openings 12, respectively, by means of hot melt adhesive 27. Preferably, the film 5 and the nonwoven fabric 26 are joined to each other also in a lower zone of the crotch region 8 by means of the hot melt adhesive 27. The film 5 is bonded to the core 4 in its zone extending in the crotch region 8 by means of hot melt adhesive 28.

Referring to FIGS. 5 and 6, the auxiliary elastic members 21 herein are sandwiched by the film 5 and the nonwoven fabric 26 to extend under tension across the diaper 1 between its opposite side edges. The uppermost one 21A of these auxiliary elastic members 21 indirectly covers the front end 22 of the absorbent core 4 inclusive of its vicinity with interposition of the film 5 so that the upper edge 31 of the member 21A lies above the front end 22 of the absorbent core 4 (See FIG. 6). The member 21A arranged in this manner advantageously tends to prevent the front end 22 of the absorbent core 4 inclusive of its vicinity from being curved outwardly of the diaper 1, i.e., away from the wearer's body as the diaper 1 is put on the wearer's body. The lowermost one 21E of these auxiliary elastic members 21 extends transversely of the diaper 1 across the crotch region 8 which extends below the front waist region 6. With the diaper 1 according to this embodiment, the members 21 comprising the uppermost and lowermost members 21A, 21E function to press the absorbent core 4 tightly against the wearer's body over an area of the absorbent core 4 as large as possible.

According to the embodiment shown in FIG. 5, the portions of the auxiliary elastic members 21 extending outward beyond the respective side edges of the absorbent core 4 are secured to the outer surface of the film 5 by means of the hot melt adhesive 27. Also when the members 21 are secured to the nonwoven fabric 26 by means of the adhesive 27 or adhesive provided separately of the adhesive 27 instead of being secured to the film 5, the same effect as achieved by bonding the members 21 to the film 5 can be achieved.

To realize the present invention, the stock material for the topsheet 2 is not limited to a nonwoven fabric and the other stock materials such as a liquid-pervious apertured plastic film may be also used for the topsheet 2. It is possible without departing from the scope of the present invention to bond the absorbent core 4 to the topsheet 2 by means of hot melt adhesive. It is also possible without departing from the scope of this invention to bond the absorbent core 4 to the backsheet 3 in any region other than the crotch region 8. When the present invention is realized in the mode as shown by FIG. 1, it is also possible to adopt an arrangement such that the front end 22 and/or the rear end 24 of the absorbent core 4 inclusive of the vicinity thereof may be directly covered with the auxiliary elastic members 21. Bonding of the respective members one to another may be performed not only by means of suitable adhesive agent such as hot melt adhesive but also by utilizing the other techniques such as heat-sealing and ultrasonic sealing.

With the disposable pull-on diaper according to the present invention, the backsheet and the liquid-absorbent core are substantially free from being finely wrinkled even when the auxiliary elastic members contract. This is for the reason that the auxiliary elastic members'are secured neither to the absorbent core nor to the backsheet over the portions of the auxiliary elastic members extending across the absorbent core. As a result, the auxiliary elastic members improve a fitting of the absorbent core to the wearer's body while the backsheet provides a smooth touch.

What is claimed is:

1. A disposable pull-on diaper comprising:
   a front waist region;
   a rear waist region;
   a crotch region located between the front waist region and the rear waist region;
   a liquid-pervious topsheet;
   a liquid-impervious backsheet; and
   a liquid-absorbent core disposed between said liquid-pervious topsheet and said liquid-impervious backsheet, said liquid-absorbent core having a width,
   said front and rear waist regions being joined to each other along transversely opposite side edges thereof so as to form a waist-opening and a pair of leg-openings,
   said waist opening being provided with a plurality of first elastic members and said leg-openings also being provided with a plurality of second elastic members, respectively,
   said first and second elastic members extending under tension along peripheral edges of said waist-opening and leg-openings,
   said disposable pull-on diaper further comprising a plurality of third elastic members which extend across said liquid-absorbent core at least in said front and rear waist regions between transversely opposite side edges of said front and rear waist regions,
   each of said plurality of third elastic members presenting a stretch stress which is lower than a stretch stress presented by each of said first elastic members, said plurality of third elastic members extending across the liquid-absorbent core on an outer surface thereof, said plurality of third elastic members having:

first portions that extend outward beyond the transversely opposite side edges of said liquid-absorbent core, said first portions being secured to said liquid-impervious backsheet; and second portions that have lengths which extend across the entire width of the liquid-absorbent core, said second portions being un-bonded to each of said liquid-impervious backsheet and said liquid-absorbent core along the entire lengths of the second portions.

2. The diaper according to claim 1, wherein said plurality of third elastic members are secured to said liquid-impervious backsheet one in a vicinity of zones in which said front and rear waist regions are bonded to each other along their respective side edges.

3. The diaper according to claim 1, wherein said liquid-impervious backsheet is made of a thermoplastic synthetic resin film and said plurality of third elastic members are secured to an inner surface of said film.

4. The diaper according to claim 1, wherein said liquid-impervious backsheet comprises thermoplastic synthetic resin film and nonwoven fabric bonded to an outer surface of said film so that said plurality of third elastic members may be disposed between said film and said nonwoven fabric and secured to the outer surface of said film of an inner surface of said nonwoven fabric.

5. The diaper according to claim 1, wherein an inner surface of said liquid-impervious backsheet is joined to the outer surface of said liquid-absorbent core.

6. The diaper according to claim 1, wherein said plurality of second elastic members are provided in the form of ribbons each having a width of about 3 to about 20 mm.

7. The diaper according to claim 1, wherein said liquid-absorbent core has front and rear ends lying in said front and rear waist regions, respectively, and upper most ones of said third elastic members cover at least one of said front and rear ends.

8. The diaper according to claim 1, wherein said absorbent core has a Gurley Stiffness Value of about 0.5 to about 2 g.

9. The diaper according to claim 1, wherein said crotch region is provided with a fourth elastic member extending under tension across said liquid-absorbent core in parallel to said plurality of third elastic members.

10. The diaper according to claim 8, wherein the combined stretch stress of the plurality of third elastic members is in the range of about 100 to about 230 gf.

* * * * *